(12) United States Patent
Pees et al.

(10) Patent No.: US 6,380,202 B1
(45) Date of Patent: Apr. 30, 2002

(54) FUNGICIDAL FLUORO-SUBSTITUTED 7-HETEROCYCLYL-TRIAZOLOPYRIMIDINES

(75) Inventors: Klaus-Juergen Pees, Mainz; Annerose Rehnig, Ingelheim; Guido Albert, Hackenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/405,658

(22) Filed: Sep. 24, 1999

Related U.S. Application Data

(60) Provisional application No. 60/101,770, filed on Sep. 25, 1998.

(51) Int. Cl.⁷ .................. A61K 31/519; C07D 487/04
(52) U.S. Cl. ................................. 514/258; 544/263
(58) Field of Search .................. 514/258; 544/254, 544/255, 263

(56) References Cited

U.S. PATENT DOCUMENTS 5,593,996 A * 1/1997 Pees et al. ............... 514/258
5,808,066 A * 9/1998 Krummel et al. ......... 544/263
5,994,360 A * 11/1999 Pfrengle .................. 514/258

* cited by examiner

*Primary Examiner*—John M. Ford
(74) *Attorney, Agent, or Firm*—Charles F. Costello

(57) ABSTRACT

The novel compounds of formula I:

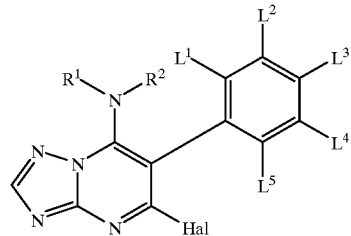

wherein ($R^1$, $R^2$, Hal and $L^1$ through $L^5$ are defined in the specification) show selective fungicidal activity and high systemicity. The new compounds are processed with carriers and adjuvants to fungicidal compositions.

9 Claims, No Drawings

FUNGICIDAL FLUORO-SUBSTITUTED 7-HETEROCYCLYL-TRIAZOLOPYRIMIDINES

This application claims benefit of Prov. No. 60/101,770 filed Sep. 25, 1998.

BACKGROUND OF THE INVENTION

This invention relates to certain triazolopyrimidine compounds having a fluoro-substituted heterocyclyl group attached to the 7-position, a process for their preparation, compositions containing such compounds, a method for combating a fungus at a locus comprising treating the locus with such compounds and their use as fungicides.

U.S. Pat. No. 5,593,996 claims compounds of the general formula

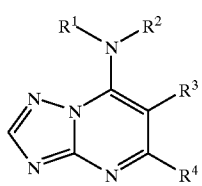

in which $R^1$ and $R^2$ together with the interjacent nitrogen atom represent an optionally substituted heterocyclic ring; $R^3$ represents an optionally substituted phenyl or naphthyl group; and $R^4$ represents a halogen atom or a group —$NR^5R^6$ where $R^5$ represents a hydrogen atom or an amino, alkyl, cycloalkyl or bicycloalkyl group and $R^6$ represents a hydrogen atom. However, there is no hint to such triazolopyrimidines, in which the heterocyclic ring formed by $R^1$ and $R^2$ with the adjacent nitrogen atom is substituted by at least one fluoro atom or fluoro alkyl group. Moreover, there is no indication that such a substitution pattern would achieve an enhancement of the systemicity of the resulting compounds.

SUMMARY OF THE INVENTION

The present invention provides a compound of formula I

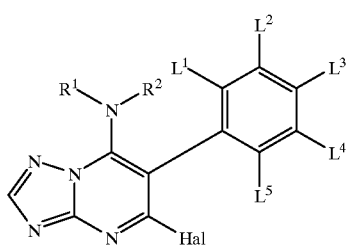

(I)

in which
- $R^1$ and $R^2$ together with the interjacent N atom represent a heterocyclic group being substituted by at least one fluorine atom or at least one fluoroalkyl group,
- Hal represents a halogen atom
- $L^1$ through $L^5$ each independently represent an hydrogen or halogen atom or an alkyl or nitro group.

The new compounds combine excellent selective fungicidal activity in various crops with high systemicity.

It is an object of the present invention to provide novel, selective fungicidal compounds.

It is also an object of the invention to provide methods for controlling an undesired fungus by contacting said plants with a fungicidally effective amount of the new compounds.

It is another object of the invention to provide selective fungicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I

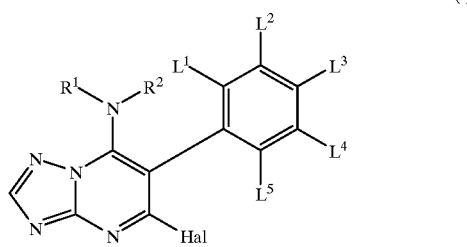

(I)

in which $R^1$, $R^2$, $L^1$ through $L^5$ and Hal have the meaning given above for formula I show an excellent fungicidal activity against a broad range of fungi and high systemicity.

In general terms, unless otherwise stated, as used herein the term halogen atom may denote a bromine, iodine, chlorine or fluorine atom, and is especially a bromine, chlorine or fluorine atom. Optionally substituted moieties may be unsubstituted or have from one up to the maximal possible number of substituents. Typically, 0 to 2 substituents are present.

In general terms, unless otherwise stated herein, the term alkyl, as used herein with respect to a radical or moiety refer to a straight or branched chain radical or moiety. As a rule, such radicals have up to 10, in particular up to 6 carbon atoms. Suitably an alkyl moiety has from 1 to 10 carbon atoms, preferably from 2 to 6 carbon atoms. A preferred alkyl moiety is an ethyl or especially a methyl group.

In general terms, unless otherwise stated herein, the term heterocyclyl, as used herein with respect to the group formed by $R^1$, $R^2$ and the interjacent nitrogen atom, refers to a nitrogen containing heterocyclyl group having 2 to 8 carbon atoms and optionally one or two oxygen or sulfur atoms, preferably 4 to 7 carbon atoms and optionally 1 oxygen atom, in particular 1H-azirid-1-yl, oxazirid-1-yl, 1H-azetid-1-yl, pyrrolid-1-yl, piperid-1-yl, piperazin-1-yl or morpholin-1-yl being substituted by one or more fluoro atoms or by one or more fluoroalkyl, preferably $C_{1-6}$ fluoroalkyl, in particular fluoromethyl groups.

Particularly preferred are those compounds of formula I, in which $R^1$ and $R^2$ together with the interjacent N atom form a group of formula

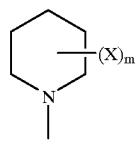

wherein
X represents a fluorine atom or a $C_{1-4}$ fluoroalkyl group, and m is an integer from 1 to 4, in particular in which m is 1 or 2 and X represents a fluorine atom or a fluoromethyl or trifluoromethyl group.

Most preferred are the 4-fluoropiperidyl, the 4,4-difluoropiperidyl, the 4-trifluoromethylpiperidyl and the 4-fluoromethylpiperidyl group.

Preferably at least one of the substituents $L^1$ through $L^5$, in particular $L^1$ and/or $L^5$, is different from hydrogen. $L^1$ is preferably a fluorine or chlorine atom or a methyl, methoxy or trifluoromethoxy group. The other substituents are preferably selected from hydrogen or fluorine.

Particularly preferred are compounds of formula I, in which the phenyl group of formula

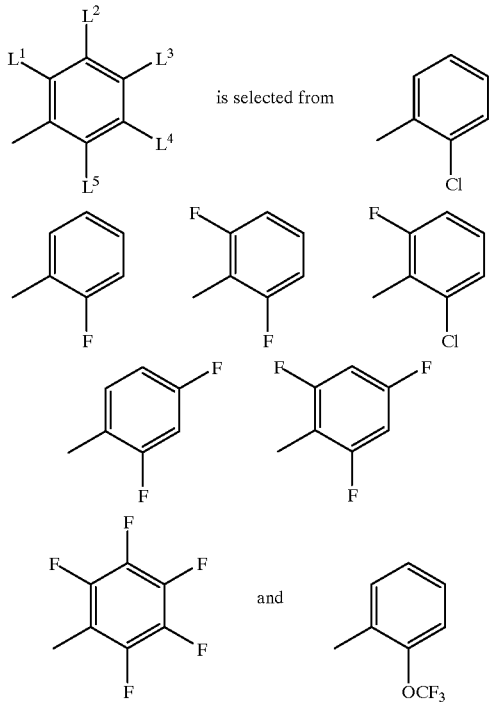

Most preferred are the 2-chloro-6-fluorophenyl and the 2,4,6-trifluorophenyl group.

The compounds according to general formula I are oils, gums, or, predominantly crystalline solid materials. They are superior through their valuable fungicidal properties, in particular their fungitoxicity against a broad range of phytopathogenic fungi. For example, they can be used in agriculture or related fields for the control of phytopathogenic fungi such as *Venturia inaequalis, Alternaria solani, Botrytis cinerea, Cercospora beticola, Cladosporium herbarum, Corticium rolfsii, Erysiphe graminis, Helminthosporium tritici repentis, Leptosphaeria nodorum, Micronectriella nivalis, Monilinia fructigena, Mycosphaerella ligulicola, Mycosphaerella pinodes, Phytophthora infestans, Puccinia recondita, Pyricularia grisea f.sp. oryzae, Rhizoctonia solani, Monographella nivalis* and *Sclerotinia sclerotiorum*, in particular for the control of *Alternaria solani, Botrytis cinerea, Erysiphe graminis, Puccinia recondita* and *Venturia inaequalis*. The compounds of general formula I according to the invention possess a high fungicidal activity within a wide concentration range and may be used in agriculture without any difficulties.

Moreover, the compounds according to the invention show enhanced systemicity and residual control of fungi compared with known triazolopyrimidine derivatives.

Good results in terms of control of phytopathogenic fungi are obtained with a compound as defined in formula I wherein:

Hal represents a chloro atom;

$R^1$ and $R^2$ together with the interjacent nitrogen atom represent a piperid-1-yl group being substituted by one fluoroalkyl, preferably straight chained or branched $C_1$–$C_3$-fluoroalkyl group, in particular fluoromethyl, or one or two fluorine atoms.

In particular preferred are the compounds of formula IA,

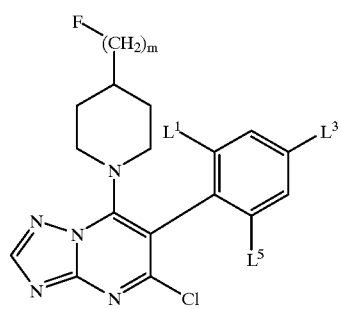

(IA)

in which $L^1$, $L^3$ and $L^5$ each independently represent hydrogen, fluorine or chlorine, methyl, trifluoromethoxy at least one of which being different from hydrogen, and m is 0 or 1.

Especially good results in terms of control of phytopathogenic fungi are obtained by using, for example, the following compounds of formula I: 5-chloro-7-N-(4-fluoropiperid-1-yl)-6-(2,4,6-trifluorophenyl)-[1,2,4]triazolo[1,5-a]pyrimidine, 5-chloro-6-(2-chloro-6-fluorophenyl)-7-N-(4-fluoromethylpiperid-1-yl)-[1,2,4]triazolo[1,5-a]pyrimidine, 5-chloro-7-N-(3-fluoropiperid-1-yl)-6-(pentafluorophenyl)-[1,2,4]triazolo[1,5-a]pyrimidine, 5-chloro-6-(2-chloro-6-fluorophenyl)-7-N-(3-fluoropiperid-1-yl)-[1,2,4]triazolo[1,5-a]pyrimidine, 5-chloro-6-(2-chloro-6-fluorophenyl)-7-N-(4,4-difluoropiperid-1-yl)-[1,2,4]triazolo[1,5-a]pyrimidine, 5-chloro-7-N-(4-fluoromethylpiperid-1-yl)-6-(2,4,6-trifluorophenyl)-[1,2,4]triazolo[1,5-a]pyrimidine, 5-chloro-6-(2-chloro-6-fluorophenyl)-7-N-(4-trifluoromethylpiperid-1-yl)-[1,2,4]triazolo[1,5-a]pyrimidine.

The present invention provides a process for the preparation of a compound of formula I, which comprises (a) treating a 5,7-dihalo-triazolopyrimidine of formula II,

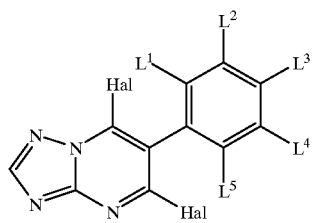

(II)

in which $L^1$ through $L^5$ and Hal are as defined in any one of the preceding claims; and with an amine of the general formula III

(III)

in which
R¹ and R² are as defined in any one of the preceding claims,
M represents a hydrogen atom or a free or complexed metal atom,
to produce a compound of formula I.

The reaction between the 5,7-dihalo-6-phenyl-triazolopyrimidines of formula II, which are known from U.S. Pat. No. 5,593,996, and the compound of formula III is conveniently carried out in the presence of a solvent. Suitable solvents include ethers, such as dioxane, diethyl ether and, especially, tetrahydrofuran, hydrocarbons such as hexane, cyclohexane or mineral oil, and aromatic hydrocarbons, for example toluene, or mixtures of these solvents. The reaction is suitably carried out at a temperature in the range from −100° C. to +120° C., the preferred reaction temperature being from −80° C. to +40° C.

The compounds of formula II are obtainable according to the methods disclosed in EP 0 770 615.

The present invention further provides a process for the preparation of a compound of formula I, which comprises (a) treating a 7-amino-5-halo-triazolopyrimidine of formula IV,

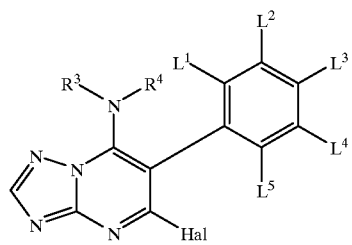

(IV)

in which
L¹ through L⁵ and Hal are as defined in any one of the preceding claims; and
R³ and R⁴ together with the interjacent N atom represent a heterocyclic group which is substituted by at least one hydroxy, oxo or hydroxyalkyl group, with a fluorination agent, such as sulfurtetrafluoride or DAST (diethylaminosulfurtriflouride).

The compounds of formula IV can be produced by treatment of a dihalotriazolopyrimidine of formula II with an amine of formula V

(V)

in which
R³ and R⁴ are as defined for formula IV, and
M represents a hydrogen atom or a free or complexed metal atom. The amines of formulae III and V are commercially available or can be prepared analogously to procedures which are known per se. The amines of formula III may be prepared by reaction of an amine of formula V with a fluorination agent as for example sulfurtetrafluoride or DAST (diethylaminosulfurtriflouride).

The compounds of general formula I have been found to have fungicidal activity. Accordingly, the invention further provides a fungicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| Active Ingredient | Compound of Example 6 | 30% (w/v) |
| Emulsifier(s) | Atlox ® 4856 B/Atlox ® 4858 B[1]  (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | to 1000 ml |
| Suspension Concentrate (SC) | | |
| Active Ingredient | Compound of Example 6 | 50% (w/v) |
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |
| Wettable Powder (WP) | | |
| Active Ingredient | Compound of Example 6 | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylaylpolyoxy acetates | 3% (w/w) |
| Carrier/Filler | Kaolin | 35% (w/w) |
| Water Dispersible Granules (WG) | | |
| Active Ingredient | Compound of Example 6 | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/Filler | Kaolin | 35% (w/w) |

[1] available from ICI Surfactants
[2] available from Deutsche Shell AG
[3] available from Rhodia (former Rhone-Poulenc)
[4] available from Kelco Co.
[5] available from Zeneca
[6] available from Witco
[7] available from International Specialty Products The compositions of this invention can also comprise other compounds having biological activity, e.g. compounds having similar or complementary pesticidal activity or compounds having plant growth regulating, fungicidal or insecticidal activity. These mixtures of pesticides can have a broader spectrum of activity than the compound of general formula I alone. Furthermore, the other pesticide can have a synergistic effect on the pesticidal activity of the compound of general formula I.

The compositions of this invention can comprise also other compounds having biological activity, e.g. compounds having similar or complementary fungicidal activity or compounds having plant growth regulating, herbicidal or insecticidal activity.

These mixtures of fungicides can have a broader spectrum of activity than the compound of general formula I alone. Furthermore, the other fungicide can have a synergistic effect on the fungicidal activity of the compound of general formula I.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, metconazole, methfuroxam, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram.

In addition, the formulations according to the invention may contain at least one compound of formula I and any of the following classes of biological control agents such as viruses, bacteria, nematodes, fungi, and other microorganism which are suitable to control insects, weeds or plant diseases or to induce host resistance in the plants. Examples of such biological control agents are: *Bacillus thuringiensis, Verticillium lecanli, Autographica californica NPV, Beauvaria bassiana, Ampelomyces quisqualis, Bacilis subtilis, Pseudomonas fluorescens, Steptomyces griseoviridis* and *Trichoderma harzianum.*

Moreover, the co-formulations according to the invention may contain at least one compound of formula I and a chemical agent that induces the systemic acquired resistance in plants such as for example nicotinic acid or derivatives thereof, 2,2-dichloro-3,3-dimethylcyclopropanecarboxylic acid or BION.

The compounds of general formula I can be mixed with soil, peat or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

Preparation of 5-chloro-7-(4-fluoropiperid-1-yl)-6-(2,4,6-trifluorophenyl)-1,2,4-triazolo[1,5a] pyrimidine A mixture 18.8 mmol DAST and dichloromethane is added to a mixture of 4.7 mmol of 5-chloro-7-(4-hydroxypiperid-1-yl)-6-(2,4,6-trifluorophenyl)-1,2,4-triazolo[1,5a]pyrimidine (obtained from 5,7-dichloro-6-(2,4,6-trifluorophenyl)-1,2,4-triazolo[1,5a]pyrimidine and 4-hydroxypiperidine) and 10 ml of dichloromethane within 30 minutes at −78° C. The resulting reaction mixture is stirred for 6 hours at −78° C., allowed to warm up to ambient temperature and stirred for further 16 hours. The reaction mixture is washed with water, the organic phase is separated, dried with sodium sulfate and the solvent is evaporated. The obtained crude product is subjected to a flash chromatography (ethyl acetate/ petrolether 1:2), which yields the product as yellow crystals (m.p. 147° C.).

EXAMPLE 2

Preparation of 5-chloro-7-(4-fluoromethylpiperid-1-yl)-6-(2-chloro-6-fluorophenyl)-1,2,4-triazolo[1,5a] pyrimidine A mixture 2.8 mmol DAST and dichloromethane is added to a mixture of 2.52 mmol of 5-chloro-7-(4-hydroxymethylpiperid-1-yl)-6-(2-chloro-6-fluorophenyl)-1,2,4-triazolo[1,5a]pyrimidine (obtained from 5,7-dichloro-6-(2-chloro-6-trifluorophenyl)-1,2,4-triazolo[1,5a]pyrimidine and 4-hydroxymethylpiperidine) and 20 ml of dichloromethane within 15 minutes at −78° C. The resulting reaction mixture is stirred for 1.5 hours at −78° C., allowed to warm up to ambient temperature and stirred for further 3 hours. The reaction mixture is washed with water, the organic phase is separated, dried with sodium sulfate and the solvent is evaporated. The obtained crude product is subjected to a flash chromatography (ethyl acetate/petrolether 1:2), which yields the product as yellow crystals (m.p. 152° C.).

EXAMPLE 3–15

The following examples (Table I; structure and melting point) are synthesized analogously to Examples 1 and 2.

TABLE I

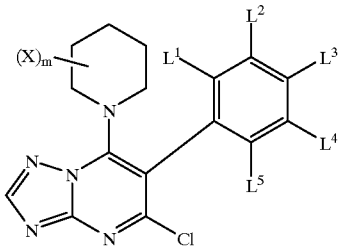

| Example | (X)$_m$ | L$^1$ | L$^2$ | L$^3$ | L$^4$ | L$^5$ | melting point (° C.) |
|---|---|---|---|---|---|---|---|
| 3 | 3-fluoro | Cl | H | H | H | F | oil |
| 4 | 3-fluoro | F | F | F | F | F | 162 |
| 5 | 4,4-difluoro | Cl | H | H | H | F | 203–204 |
| 6 | 4-fluoromethyl | F | H | F | H | F | 152 |
| 7 | 4-trifluoromethyl | F | H | H | H | Cl | 148–152 |
| 8 | 4-fluoro | F | H | H | H | F | |
| 9 | 4,4-difluoro | F | H | F | H | F | |
| 10 | 4-fluoromethyl | F | F | F | F | F | |
| 11 | 4,4-difluoro | F | F | F | F | F | |
| 12 | 4-fluoro | NO$_2$ | H | H | H | H | |
| 13 | 4-fluoromethyl | NO$_2$ | H | H | H | H | |
| 14 | 4,4-difluoro | NO$_2$ | H | H | H | H | |
| 15 | 4-fluoro | CH$_3$ | H | H | H | H | |

Biological Investigations
A In-vitro Evaluation
Determination of Minimum Inhibitory Concentration by Test Compounds in the Serial Dilution Test with Various Phytopathogenic Fungi The MIC (Minimum Inhibitory Concentration) value, which indicates the lowest concentration of the active ingredient in the growth medium which causes a total inhibition of myecelial growth, is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 mg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min. The respective inocula (Alternaria solani, ALTESO; Botrytis cinerea, BOTRCI; Leptosphaeria nodorum, LEPTNO; Phytophthora infestans, PHYTIN; Magnaporthe grisea f. sp. oryzae, PYRIOR; Pyrenophora teres, PYRNTE; Rhizoctonia solani, RHIZSO) are added into the wells as spore suspensions (50 ml; 5×10$^5$/ml) or agar slices (6 mm) of an agar culture of the fungus. After 6–12 days incubation at suitable temperatures (18–25° C.), the MIC values are determined by visual inspection of the plates (Table II).

B Greenhouse Tests
Test Diseases
(a) Wheat Powdery Mildew (WPM):
   *Erysiphe graminis* DC. f.sp. *tritici* E. Marchal
(b) Wheat Septoria nodorum (WSN):
   *Leptosphaeria nodorum*
(c) Wheat leaf rust (WLR):
   *Puccinia recondita*
Host:
   Wheat (*Triticum aestivum* L.) variety Kanzler
Test Procedure
This test procedure is for curative and residual control of wheat diseases.
1. Wheat seed (approximately 8–10/pot) is planted and maintained in the greenhouse.
2. When the primary leaf (wheat) is fully expanded, formulated test compounds are sprayed with a single nozzle overhead track sprayer at a rate of 200 l/ha (Foliar application). Alternatively, the soil in which the plants grow is drenched with the formulated test compounds (Soil drench application).
3. Inoculation precedes treatment by 2 days in the case of curative evaluations and follows treatment by 2 days in case of residual evaluations. The plants are either inoculated by dusting them with conidia from infected plants (stock cultures at an age of 10–14 days/WPM) or artificially inoculated with an aqueous spore suspension (WSN, WLR). Plants inoculated with spore suspensions are kept under high humidity conditions for up to two days and subsequently returned to the greenhouse. Between inoculation and treatment for curative evaluations and between treatment and inoculation for residual evaluations, plants are maintained in the greenhouse.
4. Disease on the primary leaf as percent leaf area with disease symptoms/signs is evaluated about 7 days after inoculation. Percent disease control is then calculated by the following formula:

$$\% \text{ disease control} = 100 - \frac{\% \text{ infection in treated plants}}{\% \text{ infection in untreated plants}} \times 100$$

Formulation, Reference Compounds and Controls
1. Technical compounds are formulated in a solvent/surfactant system consisting of 5% acetone and 0.05% Triton X 155 in deionized water. Compounds are dissolved in acetone prior to addition of the water. Dilutions are made using the solvent/surfactant system. Formulated compounds are prepared using deionized water.
2. Two kinds of controls are included:
   Plants treated with the solvent/surfactant solution and inoculated (Solvent Blank); Untreated plants which are inoculated (Inoculated Control).
   The results of this evaluation are shown in Tables III and IV:

TABLE II

| Example | ALTESO | BOTRCI | LEPTNO | PHYTIN | PYRIOR | PYRNTE | RHIZSO |
|---|---|---|---|---|---|---|---|
| 1 | 0.2 | 3.13 | 12.5 | 50 | 1.56 | 1.56 | 12.5 |
| 2 | 0.39 | 3.13 | >100 | >100 | 0.78 | 3.13 | >100 |
| 3 | 6.25 | 12.5 | 50 | >100 | 6.25 | 6.25 | 50 |
| 4 | 3.13 | 12.5 | 50 | 100 | 1.56 | 12.5 | 6.25 |
| 5 | <0.05 | 50 | 12.5 | >100 | 0.2 | 3.13 | >100 |
| 6 | 0.39 | 3.13 | >100 | >100 | 0.78 | 3.13 | >100 |

TABLE III

Curative and Residual Fungicidal activity of compounds of formula I (Foliar application)

| Disease Test | Rate (ppm) | Disease control (% efficacy) Example | | | | | |
|---|---|---|---|---|---|---|---|
| | | 1 | 2 | 3 | 4 | 5 | 6 |
| WPM | 100 | 100 | 96 | 100 | 92 | 94 | 100 |
| 2 da R | 25 | 100 | 0 | 98 | 0 | 84 | 63 |
| | 6.3 | 88 | 0 | 0 | 0 | 74 | 0 |
| WSN | 100 | 100 | 83 | 92 | 0 | 98 | 99 |
| 2 da R | 25 | 54 | 17 | 0 | 0 | 36 | 63 |
| | 6.3 | 0 | 0 | 0 | 0 | 0 | 0 |
| WLR | 100 | 100 | 100 | 100 | n.t. | 94 | 100 |
| 2 da R | 25 | 95 | 100 | 96 | n.t. | 62 | 100 |
| | 6.3 | 22 | 100 | 42 | n.t. | 0 | 100 |
| WLR | 100 | 100 | 100 | 100 | 53 | 10 | 100 |
| 2 da C | 25 | 81 | 90 | 60 | 0 | 0 | 100 |
| | 6.3 | 0 | 28 | 0 | 0 | 0 | 98 |

2 da C = 2 day curative Inoculation 2 days BEFORE application
2 da R = 2 day residual Inoculation 2 days AFTER application

TABLE IV

Comparison of the Residual Fungicidal activity of compounds of formula I in Soil drench application with a known triazolopyrimidene (Standard)

| Disease Test | Rate (ppm) | Disease control (% efficacy) Example | | |
|---|---|---|---|---|
| | | 1 | 6 | Standard[1] |
| WLR | 200 | 100 | 100 | 0 |
| 2 da R | 50 | 98 | 100 | 0 |

[1]5-chloro-7-(4-methylpiperid-1-yl)-6-(2-chloro-6-fluorophenyl)-1,2,4-triazolo[1,5a]pyrimidine which is known from U.S. Pat. No. 5,593,996

What is claimed is:

1. A compound of formula I

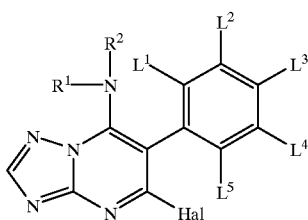

in which $R^1$ and $R^2$ together with the interjacent N atom form a group having the formula

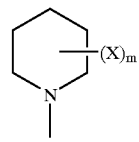

wherein

X represents a fluorine atom or a $C_{1-4}$ fluoroalkyl group, and m is an integer from 1 to 4, Hal represents a halogen atom, and $L^1$ is a fluorine or chlorine atom, $L^2$ and $L^4$ is a hydrogen atom, and $L^5$ is a fluorine atom.

2. A compound according to claim 1 in which X represents a fluorine atom or a fluoromethyl or trifluoromethyl group and m is 1 or 2.

3. A compound selected from the group consisting of 5-chloro-7-N-(4-fluoropiperid-1-yl)-6-(2,4,6-trifluorophenyl)-[1,2,4]triazolo[1,5-a]pyrimidine, 5-chloro-6-(2-chloro-6-fluorophenyl)-7-N-(4-fluoromethylpiperid-1-yl)-[1,2,4]triazolo[1,5-a]pyrimidine, 5-chloro-7-N-(3-fluoropiperid-1-yl)-6-(pentafluorophenyl)-[1,2,4]triazolo[1,5-a]pyrimidine, 5-chloro-6-(2-chloro-6-fluorophenyl)-7-N-(3-fluoropiperid-1-yl)-[1,2,4]triazolo[1,5-a]pyrimidine, 5-chloro-6-(2-chloro-6-fluorophenyl)-7-N-(4,4-difluoropiperid-1-yl)-[1,2,4]triazolo[1,5-a]pyrimidine, 5-chloro-7-N-(4-fluoromethylpiperid-1-yl)-6-(2,4,6-trifluorophenyl)-[1,2,4]triazolo[1,5-a]pyrimidine, and 5-chloro-6-(2-chloro-6-fluorophenyl)-7-N-(4-trifluoromethylpiperid-1-yl)-[1,2,4]triazolo[1,5-a]pyrimidine.

4. A fungicidal composition which comprises a carrier, and as an active agent, one or more compounds of formula I as defined in claim 2 or 3 or 1.

5. A method of combating phytopathogenic fungus at a locus which comprises treating the locus with an effective amount of a compound of formula I as defined in claim 2 or 3 or 1.

6. A method of combating phytopathogenic fungus at a locus which comprises treating the locus with an effective amount of a composition as defined in claim 4.

7. A compound according to claim 2 in which X represents the fluoromethyl or trifluoromethyl group.

8. A compound according to claim 7 in which X is a trifluoromethyl group.

9. A compound of formula I in which $R^1$ and $R^2$ together with the interjacent N atom represent a heterocyclic group having 4 to 7 carbon atoms being substituted by one or more fluorine atoms or fluoroalkyl groups, Hal represents a halogen atom, and $L^1$ is a fluorine or chlorine atom, $L^2$ and $L^4$ is a hydrogen atom, and $L^5$ is a fluorine atom.

* * * * *